US00PP28754P3

(12) United States Plant Patent
Bacon

(10) Patent No.: US PP28,754 P3
(45) Date of Patent: Dec. 12, 2017

(54) APRICOT TREE NAMED 'SUAPRIFOURTEEN'

(50) Latin Name: *Prunus armeniaca*
Varietal Denomination: Suaprifourteen

(71) Applicant: Sun World International, LLC, Bakersfield, CA (US)

(72) Inventor: Terry A. Bacon, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 110 days.

(21) Appl. No.: 14/998,451

(22) Filed: Jan. 5, 2016

(65) Prior Publication Data

US 2017/0196134 P1 Jul. 6, 2017

(51) Int. Cl.
*A01H 5/08* (2006.01)

(52) U.S. Cl.
USPC ..... Plt./186

(58) Field of Classification Search
USPC ..... Plt./156, 180, 186
See application file for complete search history.

*Primary Examiner* — Susan McCormick Ewoldt
*Assistant Examiner* — Karen Redden
(74) *Attorney, Agent, or Firm* — Knobbe, Martens, Olson & Bear, LLP

(57) ABSTRACT

A new and distinct apricot tree, *Prunus armeniaca* cv. 'Suaprifourteen' is characterized as a productive mid-season variety with fruit size of approximately 92 gm, a high degree of red overcolor covering about 30% of the surface, and a high sugar content of about 18° brix.

1 Drawing Sheet

Latin name of the genus and species claimed: *Prunus armeniaca.*

Variety denomination: 'Suaprifourteen'.

BACKGROUND AND SUMMARY OF THE INVENTION

The present invention relates to a new and distinct variety of apricot tree, herein after referred to by the cultivar name 'Suaprifourteen'. The new variety was first originated by hybridized in May 2012 by Terry A. Bacon as breeder number: 'AP1440'.

The new variety is characterized as a productive mid-season variety with fruit size of approximately 92 gm, a high degree of red overcolor covering about 30% of the surface, and a high sugar content of about 18° brix.

The seed parent is 'AP540' (unpatented breeding selection), and the pollen parent is 'BSCot2' (unpatented breeding selection). The parent varieties were first crossed in February 2008, with the date of first sowing being February 2009, and the date of first flowering being February 2011. The new apricot variety 'Suaprifourteen' was first asexually propagated by Terry Bacon near Wasco, Kern County, Calif. in January 2013 by grafting.

The new variety 'Suaprifourteen' can be distinguished from its seed parent, 'AP540' (unpatented breeding selection) in that harvest of fruit from the new variety 'Suaprifourteen' starts later at about May 14, compared to about May 5 for 'AP540'. The new variety 'Suaprifourteen' also has a higher degree Brix at 18° compared to 13° for 'AP540'.

The new variety 'Suaprifourteen' is similar to its pollen parent, 'BSCot2' (unpatented breeding selection) in that the fruit of each variety ripens at about the same time. The new variety 'Suaprifourteen' can be distinguished from 'BSCot2' in that it has a smaller fruit size at about 92 g compared to about 117 g for the fruit of 'BSCot2'. The new variety 'Suaprifourteen' has a higher degree Brix at 18° compared to 14° for 'BSCot2'. The new variety 'Suaprifourteen' also has a bright orange background color compared to dull greenish for 'BSCot2'.

The fruit of the new variety 'Suaprifourteen' ripens at about the same time as the fruit of 'Suapriseven' (U.S. Plant Pat. No. 10,165) and the fruit size is also similar. However, fruit of the new variety 'Suaprifourteen' has a higher Brix at 18° compared to 15° for 'Suapriseven'. Additionally, the fruit of the new variety 'Suaprifourteen' has a lower acidity of 1.3% TA compared to 2.3% TA for 'Supriseven' and a higher percent blush at 30% compared to 20% for 'Supriseven'. The fruit of the new variety 'Suaprifourteen' ripens at about the same time as 'Castlebrite' (unpatented) but has a higher Brix of 18° compared to 13° for 'Castlebrite'. Moreover, the fruit of the new variety 'Suaprifourteen' has a higher blush at 30% compare to 0% for the fruit of 'Castlebrite'.

The new variety 'Suaprifourteen' has been shown to maintain its distinguishing characteristics through successive asexual propagations by, for example, grafting.

BRIEF DESCRIPTION OF THE PHOTOGRAPH

The accompanying color photographic illustration shows typical specimens of the foliage and fruit of a 4 year old plant of the present new apricot variety 'Suaprifourteen'. The illustration shows the upper and lower surface of the leaves, a view of the fruit as a whole, and a sectional view of a fruit divided across its suture plane to show flesh color, pit cavity and the stone remaining in place. The photographic illustration was taken shortly after the fruit was picked and the colors are as nearly true as is reasonably possible in a color representation of this type.

DETAILED DESCRIPTION OF THE PREFERRED EMBODIMENT

Throughout this specification, color names beginning with a small letter signify that the name of that color as used in common speech is aptly descriptive. Color names beginning with a capital letter designate values based upon The R.H.S. Colour Chart published by The Royal Horticultural Society, London, England, 1986.

The descriptive matter which follows pertains to 3 year old 'Suaprifourteen' plants grown in the vicinity of Wasco, Kern County, Calif., during 2015 and is believed to apply to plants of the variety grown under similar conditions of soil and climate elsewhere.

TREE

General: (Measurements taken on 3 year old trees unless otherwise noted).

*Tree size*.—Medium. Reaches a height of 3.5 meters with normal pruning.

*Spread*.—3 meters.

*Tree vigor*.—Medium-high. Growth of approximately 2 meters height the first growing season.

*Tree growth*.—Semi-upright.

*Tree productivity*.—Productive; sets two or more times the final number of fruit. About 700 25 lb cartons of fruit are obtained per acre for mature trees trained in a traditional California vase at 170 trees/acre.

*Tree form*.—Vase formed.

*Bearer*.—Regular.

*Fertility*.—Unknown.

*Tree canopy density*.—Medium. Pruning is required to open tree vase shape, allowing more sunlight to reach the center of the tree.

*Tree hardiness*.—Hardy in all fruit-growing areas of California. Winter chilling requirement is approximately 500 hours at or below 7.2° C.

*Tree disease resistance/susceptibility*.—No specific testing for relative plant disease resistance/susceptibility has been undertaken. Under close observation in the area of Wasco, Kern County, Calif., no particular plant/fruit disease resistance/susceptibility has been observed.

Trunk: (Measurements at 30 cm above soil line).

*Trunk diameter*.—Approximately 21 cm.

*Trunk texture*.—Moderately shaggy.

*Trunk color* (*outer bark*).—About Medium Greyed-Green 198B and Light Greyed-Green 198D, with areas of Medium Greyed-Orange 176A.

*Trunk color* (*inner bark*).—About Light Greyed-Orange 174C and Medium Greyed-Orange 174A.

Branches: (Measurements at approximately 90 cm above soil line).

*Branch diameter*.—Approximately 3 cm.

*Branch texture*.—Smooth on 1$^{st}$ year wood, increasing roughness with tree age.

*Branch color*.—About Medium Greyed-Orange 173A with Light Orange-White 159D in more exposed areas.

*Branch lenticels*.—Few. Size: Medium. Density (no./cm$^2$): Variable, about 5/cm$^2$. Color: About Light Orange-White 159D. Typical size: Approximately 4 mm in length and approximately 2 mm wide.

Flowering shoots: (Data taken in July at midpoint of current-season growth. Color and sizes described may vary due to differences in sunlight, vigor and temperatures.).

*Flowering shoot diameter*.—Approximately 6 mm.

*Flowering shoot color*.—Topside: About Dark Greyed-Purple 187A. Underside: About Dark Greyed-Purple 187A.

*Flowering shoot lenticels*.—Amount: Sparse. Color: About Dark Greyed-White 156A. Diameter: Approximately 0.5mm.

*Flowering shoot leaf buds*.—Shape: Ovoid. Width: Approximately 1.5 mm. Length: Approximately 2 mm. Color: About Dark Greyed-Orange 165A.

*Flowering shoot flower buds*.—Shape: Elongated ovoid. Width: Approximately 1.5 mm. Length: Approximately 4 mm. Color: About Dark Greyed-Orange 165A Number: Usually 2.

*Internode length*.—Medium and variable, approximately 1-4 cm midway on flowering shoots.

*Density of buds*.—Medium.

*Distribution*.—Generally isolated on spurs and one year old shoots and older wood.

*Ration of wood* (*leaf*) *bud to flowering shoots*.—1/2.

FOLIAGE

Leaves: (Data taken in July on fully expanded leaf at midpoint of current-season growth. Color and sizes described may vary due to differences in sunlight, vigor and temperatures).

*Leaf size*.—Large. Length: Medium, approximately 90 mm. Width: Medium, approximately 83 mm.

*Leaf thickness*.—Medium, typical of *Prunus armeniaca*.

*Leaf color*.—Upper surface: About Dark Green 131A. Lower surface: About Medium Green 137C.

*Leaf form*.—Circular.

*Leaf tip*.—Mucronate.

*Leaf base*.—Rounded.

*Leaf margin*.—Crenate.

*Venation*.—Pinately net veined.

*Vein color*.—About Medium Green 138B.

*Leaf surface texture*.—Smooth on lower and upper surfaces.

*Leaf blade* (*ratio length/width*).—Small.

*Shape in cross section*.—Flat.

*Angle at apex*.—Small.

*Profile*.—Flat.

*Leaf blade tip*.—In the plane of the leaf.

*Undulation of margin*.—Slight.

*Arrangement of leaves*.—Alternate.

Petiole:

*Length*.—Long, approximately 24 mm.

*Diameter*.—Approximately 2 mm.

*Color*.—About Medium Green 138B, becoming Medium Greyed-Red 181A in sunlight.

*Texture*.—Smooth.

Stipules:

*Number/leaf bud*.—Approximately 0 to 2.

*Typical length*.—Approximately 7 mm.

*Color*.—About Medium Green 139C.

*Persistence*.—Fall off.

*Texture*.—Smooth.

Glands:

*Form*.—Globose.

*Number*.—Approximately 0 to 3, usually 3.
*Position*.—On petiole, usually opposite, with occasional single gland.
*Size*.—Medium, approximately 0.6 mm.
*Color*.—About Dark Greyed-Purple 183A.

FLOWERS

General:
*First bloom*.—February 21.
*Location of first bloom*.—Upper portion of the canopy.
*Full bloom*.—February 25.
*Location of full bloom*.—Middle of the canopy.
*Time of bloom*.—Medium, typical for commercial apricots in San Joaquin Valley, Calif.
*Duration of bloom*.—Medium, about 10 days.
*Diameter of fully open flower*.—Medium, approximately 25 mm to 35 mm, usually about 32 mm.
*Flower aroma*.—Very slight.
*Shape*.—Rosaceous.
Peduncle:
*Length*.—Medium, approximately 3 mm.
*Diameter*.—Medium, approximately 2 mm.
*Color*.—About Light Yellow-Green 145C, with highlights of about Medium Red 46D.
*Pubescence*.—Absent.
Petals:
*Number*.—5.
*Arrangement*.—Overlapping.
*Length*.—Approximately 12 mm.
*Diameter*.—Approximately 10 mm.
*Shape*.—Circular.
*Apex shape*.—Rounded.
*Base shape*.—Narrows at point of attachment.
*Color*.—Inner Surface: About Light Red 36D. Outer Surface: About Light Red 36D.
*Surface texture*.—Smooth on lower and upper surfaces.
*Margins*.—Smooth and slightly undulating.
*Frequency of flowers with double petals*.—None.
*Margin waviness*.—Weak.
*Base angle*.—Wide.
*Pubescence of inner surface*.—Absent.
*Pubescence of outer surface*.—Absent.
Sepals:
*Number*.—5.
*Length*.—Approximately 6 mm.
*Diameter*.—Approximately 4.5 mm.
*Shape*.—Broad ovate.
*Color*.—About Medium Red 43B.
*Surface texture*.—Smooth.
*Margins*.—Entire.
*Positioning*.—Adpressed to petals when first opened, folding back against receptacle as flower nears petal fall.
*Pubescence of inner surface*.—Absent.
*Pubescence of outer surface*.—Absent.
*Frequency of flowers with double sepals*.—None.
Stamens:
*Number*.—Approximately 25.
*Length*.—Approximately 7 mm to 12 mm, average 10 mm.
*Filament color*.—About White 155A.
*Anther color*.—About Medium Yellow 11A.
*Pollen color*.—About Medium Yellow 11A.
*Position*.—Perigynous.
Pistil:
*Number*.—Usually one.
*Average length*.—Approximately 8 mm.
*Ovary diameter*.—Approximately 3 mm.
*Pubescence*.—Medium.
*Stigma extension in comparison to anthers*.—Below the anthers.
*Frequency of supplementary pistils*.—Few.
Receptacle:
*Depth*.—Medium, approximately 4 mm.
*Pubescence of inner surface* (*at pink bud stage*).—Absent.
*Pubescence of outer surface*.—Absent.

FRUIT (Data taken at firm-ripe on 3 year old tree managed to obtain maximum quality under conditions stated in Description of Variety. Timing, colors and sizes described may vary due to differences in sunlight, vigor and temperatures).
General:
*Fruit harvest*.—Date of First Pick: Approximately May 15. Date of Mid-Harvest: Approximately May 19. Date of Last Pick: Approximately May 25.
*Date of description*.—Approximately May 19.
*Maturity when described*.—Firm-mature.
*Season ripening*.—Mid-season for apricots in central San Joaquin Valley, Calif.
*Position of maximum diameter*.—Towards the middle.
*Symmetry about the suture*.—Nearly symmetrical.
Fruit size:
*Length* (*stem end to apex*).—Approximately 55 mm.
*Diameter in line with suture plane*.—Approximately 54 mm.
*Diameter perpendicular to suture plane*.—Approximately 56 mm.
*Average weight*.—Approximately 92 gm.
Fruit apex shape: Slightly indented at tip.
Fruit apex base: Rounded.
Fruit stem cavity:
*Shape*.—Rounded.
*Depth*.—Medium, approximately 10 mm.
*Breadth*.—Approximately 15 mm.
Fruit stem:
*Length*.—Medium, Approximately 8 mm.
*Diameter*.—Approximately 2 mm.
*Color*.—About Medium Green 143C.
*Adherence to stone*.—Usually free from stone.
Fruit skin:
*Thickness*.—Medium, typical of commercial apricots.
*Adherence to flesh*.—Medium.
*Surface texture*.—Smooth, slightly pubescent.
*Pubescence*.—Scant, short, does not need roll up when rubbed.
*Bloom*.—Absent.
*Ground color*.—About Dark Orange 26A.
*Overcolor*.—About Medium Red 45C, covering about 30% of surface.
*Taste*.—Mildly tart.
*Reticulation*.—Absent.
*Tendency to crack*.—Slight, in wet seasons.
Fruit flesh:
*Ripens*.—Evenly.
*Texture*.—Melting.
*Fibers*.—Few.

*Flavor*.—Sweet-mild and aromatic.
*Sugar content*.—High, Brix 18°.
*Brix acid ratio*.—Approximately 13.85.
*Juice*.—Abundant to moderate.
*Acidity*.—Medium, about 1.3%
*Aroma*.—Abundant.
*Firmness*.—Firm, about 7 lbf.
*Color*.—About Dark Orange 26A.
*Anthocyanin color under skin*.—Absent.
*Anthocyanin color of flesh*.—Absent.
*Anthocyanin color around stone*.—Absent.

Pit cavity size:
*Length*.—Approximately 30 mm.
*Diameter in line with suture plane*.—Approximately 24 mm.
*Diameter perpendicular to suture plane*.—Approximately 12 mm.
*Color*.—About Dark Orange 26A.

Fruit shipping/keeping quality: Medium.
Market use of fruit: Fresh market.

Stone:
*Stone freeness*.—Free.
*Degree of adherence to flesh*.—Medium.
*Size*.—Medium. Length: Medium, approximately 28 mm. Diameter in Line with Suture Plane: Approximately 22 mm. Diameter Perpendicular to Suture Plane: Approximately 11 mm.
*Stone/flesh ration*.—4 g/92 g.
*Size compared to fruit*.—Small.
*Stone form* (*viewed from side*).—Round-elongated.
*Stone form* (*viewed from stem end*).—Oval, narrow.
*Stone base shape*.—Rounded.
*Stone apex shape*.—Nearly rounded.
*Hilum*.—Narrow, approximately 3 mm.
*Stone surface*.—Slightly pitted throughout with two distinct continuous ridges on either side of ventral edge.
*Stone outgrowing keel*.—Partly developed.
*Stone tendency to split*.—Rare.
*Stone color*.—About Medium Greyed-Orange 164C.
*Position of maximum*.—Middle.
*Sides*.—Nearly equal.
*Pits*.—Shallow, somewhat regular throughout.
*Fibers*.—Absent or not noticeable.
*Ventrical edge*.—Thin with slight wing towards middle.
*Dorsal edge*.—Thin, continuous and rounded.

What is claimed is:

1. A new and distinct variety of apricot tree named 'Suaprifourteen' as herein illustrated and described.

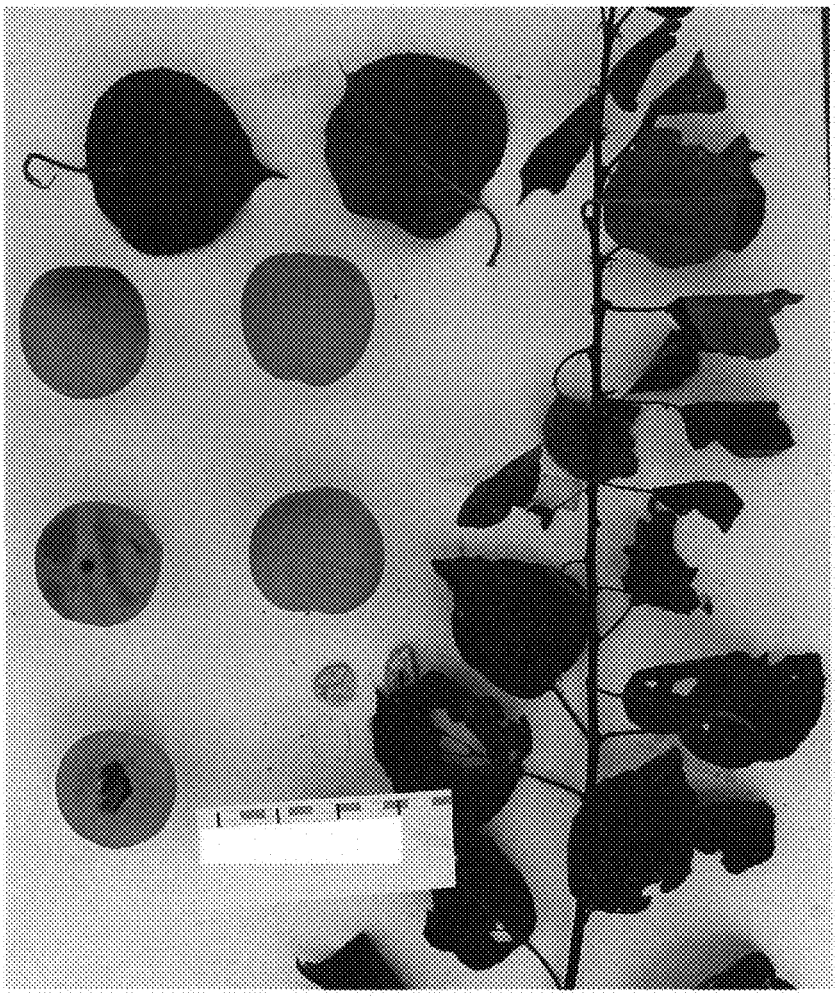

* * * * *